US007671204B2

(12) United States Patent
Wang et al.

(10) Patent No.: US 7,671,204 B2
(45) Date of Patent: Mar. 2, 2010

(54) N-DEMETHYLATION OF N-METHYL MORPHINANS

(75) Inventors: Peter X. Wang, Clarkson Valley, MO (US); Tao Jiang, St. Louis, MO (US); Gary L. Cantrell, Troy, IL (US); David W. Berberich, St. Peters, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 12/316,821

(22) Filed: Dec. 17, 2008

(65) Prior Publication Data

US 2009/0156815 A1 Jun. 18, 2009

Related U.S. Application Data

(60) Provisional application No. 61/014,086, filed on Dec. 17, 2007.

(51) Int. Cl.
*C07D 489/02* (2006.01)
*C07D 489/00* (2006.01)

(52) U.S. Cl. .............................. 546/46; 546/43; 546/44

(58) Field of Classification Search .................. 546/46, 546/44, 43
See application file for complete search history.

(56) References Cited

U.S. PATENT DOCUMENTS

| 3,299,072 A | 1/1967 | Bartels-Keith |
| 4,368,326 A | 1/1983 | Rice |
| 6,790,959 B1 | 9/2004 | Lin et al. |
| 2004/0108090 A1 | 6/2004 | Boyle |

FOREIGN PATENT DOCUMENTS

FR 1 602 610 1/1971

WO WO 03/018588 3/2003

OTHER PUBLICATIONS

Schwartz et al., "Oxidative coupling of cis-3,N-bis(methoxycarbonyl)-N-norreticuline. An approach to the asymmetric synthesis of morphine alkaloids", Journal of Organic Chemistry, 1988, vol. 53, No. 10, pp. 2318-2322, XP002518505.
Birch et al., "Lateral control of skeletal rearrangement by complexation of thebaine with Fe(CO)3", Tetrahedron Letters, 1985, vol. 26, No. 4, pp. 501-504, XP002518373.
Schwartz et al., "Biomimetic approaches to morphine alkaloids. Total synthesis of (.+-.)-2-hydroxycodeine and (.+-.)-noroxycodone", Journal of Organic chemistry, 1981, vol. 46, No. 22, pp. 4623-4625, XP002518506.
Database CA [Online] Chemical Abstracts Service, 1999, Coop et al., "A novel synthesis of thebaine from codeine", XP002518374.
Database CA [Online] Chemical Abstracts Service, 1990, Schwartz et al., "Oxidative coupling of cis-3,N-bis(methoxycarbonyl)-N-norreticuline. An approach to the asymmetric synthesis of morphine alkaloids", XP002518375.
Database CA [Online] Chemical Abstracts Service, 1985, Kirby et al., "Synthesis of 14.beta.-mercaptocodeinone derivatives from N-tert-butoxycarbonyl-N-northebaine", XP002518377.
Database CA [Online] Chemical Abstracts Service, 1983, Bladon et al., "Formation of aziridinones (.alpha.-lactams) from hydroxamic derivatives", XP002518378.
Database CA [Online] Chemical Abstracts Service, 1966, Bartels & Keith, "Syntheses related to northebaine. I. Northbaine and N-allylnorthebaine", XP002518380.
Database CA [Online] Chemical Abstracts Service, 1964, "Synthesis of N-alllylnorthebaine", XP002518381.
Search Report of the ISA with mailing date Mar. 19, 2009.

*Primary Examiner*—Charanjit S Aulakh
(74) *Attorney, Agent, or Firm*—Craig D. Siman

(57) ABSTRACT

The present invention provides a synthetic process for the N-demethylation of N-methyl morphinans. In particular, the invention provides improved synthetic methods for the preparation of N-demethylated morphinan compounds that may be employed as starting materials, for example, commonly available N-methyl opiates such as oripavine and thebaine, and C(3)-protected hydroxy derivatives of oripavine.

18 Claims, No Drawings

N-DEMETHYLATION OF N-METHYL MORPHINANS

CROSS-REFERENCE TO RELATED APPLICATION

This application claims priority from Provisional Application Ser. No. 61/014,086 filed on Dec. 17, 2007, which is hereby incorporated by reference in its entirety.

FIELD OF THE INVENTION

The present invention generally relates to the N-demethylation of N-methyl morphinans.

BACKGROUND OF THE INVENTION

Commercially valuable "nal" morphinan compounds or intermediates, such as naltrexone, naloxone, nalbuphene, nalmefene, and buprenorphine, are generally prepared from nor-morphinan compounds that lack substitution on the nitrogen atom of the heterocyclic ring. These nor-morphinan compounds may be derived from natural opiates or derivatives, such as thebaine and oripavine. This approach, however, requires removal of the N-methyl substituent, an approach that can lead to a complex mixture of products. There is a need, therefore, for improved synthetic methods for the preparation of N-demethylated morphinan compounds.

SUMMARY OF THE INVENTION

Among the various aspects of the present invention may be noted the provision of improved synthetic methods for the preparation of N-demethylated morphinan compounds that may employ as starting materials, for example, commonly available N-methyl opiates such as oripavine and thebaine, and C(3)-protected hydroxy derivatives of oripavine.

One aspect of the invention encompasses a process for preparing a compound comprising Formula 2 from a compound comprising Formula 1 according to the following reaction:

Reaction Scheme 1

[Structure (1)] → Proton Acceptor and LC(O)OZ or C(O)NZ$_2$ → [Structure (2)]

wherein:
R$^1$ is selected from the group consisting of hydrogen, hydrocarbyl, and substituted hydrocarbyl;
R$^2$, R$^3$, and R$^4$ are independently selected from the group consisting of hydrogen, halogen, hydroxyl, {—}OR$^8$, hydrocarbyl, and substituted hydrocarbyl;
R$^6$ is an atom selected from the group consisting of oxygen and nitrogen;
R$^8$ is selected from the group consisting of hydrocarbyl and substituted hydrocarbyl;
L is halogen;
Y is an atom selected from the group consisting of oxygen, nitrogen and sulfur;
Z is selected from the group consisting of hydrocarbyl and substituted hydrocarbyl; and
n is 1 or 2.

A further aspect of the invention provides an N-carboxylic acid ester morphinan derivative comprising Formula 2:

[Structure (2)]

wherein:
R$_3$ is selected from the group consisting of methyl, —C(O)OZ, and a hydroxy protecting group, and
Z is selected from the group consisting of hydrocarbyl and substituted hydrocarbyl.

Other aspects and iterations of the invention are described in more detail below.

DETAILED DESCRIPTION OF THE INVENTION

A process has been discovered for the N-demethylation of a variety of N-methyl morphinan compounds. In particular, the process comprises replacing the N-methyl substituent of an N-methyl morphinan substrate with a carboxylic acid ester substituent or a carboamide substituent to form an N-carboxylic acid ester morphinan derivative or an N-carboamide morphinan derivative, respectively. The resulting N-carboxylic acid ester or N-carboamide derivative may then be converted to yield other morphinan derivatives such as, for example, the opiate antagonist, naltrexone or naloxone.

I. N-Demethylation Reaction

For purposes of illustration, Reaction Scheme 1 depicts the N-demethylation of N-methyl morphinan substrate (1) and the formation of an N-substituted morphinan derivative (2) in accordance with one aspect of the present invention:

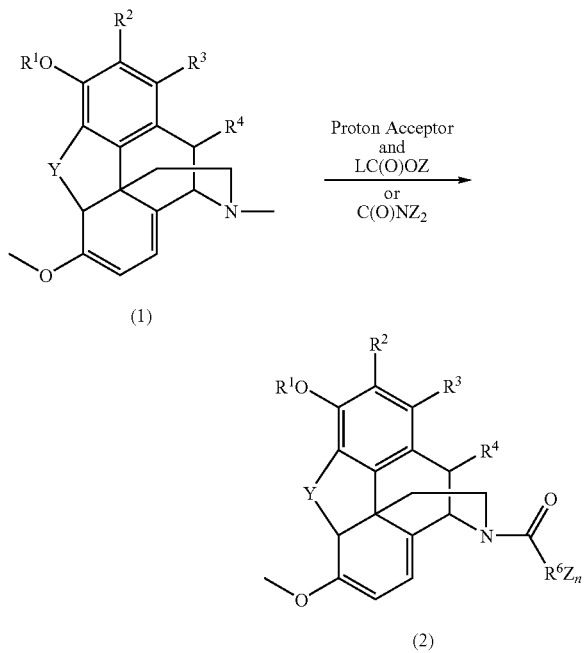

Reaction Scheme 1 wherein:
- $R^1$ is selected from the group consisting of hydrogen, hydrocarbyl, and substituted hydrocarbyl;
- $R^2$, $R^3$, and $R^4$ are independently selected from the group consisting of hydrogen, halogen, hydroxyl, {—}$OR^8$, hydrocarbyl, and substituted hydrocarbyl;
- $R^6$ is an atom selected from the group consisting of oxygen and nitrogen;
- $R^8$ is selected from the group consisting of hydrocarbyl and substituted hydrocarbyl;
- L is halogen;
- Y is an atom selected from the group consisting of oxygen, nitrogen, and sulfur;
- Z is selected from the group consisting of hydrocarbyl and substituted hydrocarbyl; and
- n is 1 or 2.

In a preferred embodiment, the substituents of Reaction Scheme 1 comprise:
- $R^1$ is selected from the group consisting of hydrogen, alkyl, alkenyl, aryl, substituted alkyl, substituted alkenyl, substituted aryl, acyl, alkoxycarbonyl, acetal, ether, silyl ether, and alkylsulfonyl;
- $R^2$, $R^3$, and $R^4$ are independently selected from the group consisting of hydrogen, halogen, hydroxyl, acyl, alkyl, alkenyl, aryl, substituted alkyl, substituted alkenyl, substituted aryl, and alkoxycarbonyl;
- $R^6$ is selected from the group consisting of oxygen and nitrogen;
- L is selected from the group consisting of chloro and bromo;
- Y is oxygen;
- Z is selected from the group consisting of alkyl, alkenyl, alkylaryl, aralkyl, aryl, substituted alkyl, substituted alkenyl, substituted alkylaryl, substituted aralkyl, and substituted aryl; and
- n is 1 or 2.

In a further iteration of this embodiment, $R^1$ is selected from the group consisting of hydrogen, methyl, alkyl, acyl, alkoxycarbonyl, and alkylsulfonyl. In an exemplary iteration of this embodiment, Z is selected from the group consisting of methyl, ethyl, propyl, isopropyl, butyl, isobutyl, tert-butyl, phenyl, benzyl, methoxymethyl, vinyl, and 2-chloroethyl.

The process of the invention comprises treating an N-methyl morphinan substrate (compound 1) with a demethylating agent to form an N-substituted morphinan (compound 2). In general, the substrate for the N-demethylation reaction (compound 1) may be any N-methyl morphinan compound. In preferred embodiments, compound 1 may be thebaine, oripavine, or a derivative of each of these compounds. When compound 1 comprises thebaine, $R^1$ is methyl, $R^2$, $R^3$, and $R^4$ are each hydrogen, and Y is oxygen. Alternatively, when compound 1 comprises oripavine, $R^1$ is hydrogen, $R^2$, $R^3$, and $R^4$ are each hydrogen, and Y is oxygen. One of skill in the art will appreciate that the oxygen attached to C(3) of oripavine or another N-methyl morphinan substrate may be protected with an oxygen protecting group.

The oxygen protecting group may be alkoxycarbonyl, acyl, acetal, ether, ester, silyl ether, alkylsulfonyl, or arylsulfonyl. Exemplary oxygen protecting groups include allyl, triphenylmethyl (trityl or Tr), benzyl, methanesulfonyl, p-toluenesulfonyl, p-methoxybenzyl (PMB), p-methoxyphenyl (PMP), methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM), benzoate (Bz), allyl carbonate, 2,2,2-trichloroethyl carbonate (Troc), 2-trimethylsilylethyl carbonate, trimethylsilyl (TMS), triethylsilyl (TES), triisopropylsilyl (TIPS), triphenylsilyl (TPS), t-butyldimethylsilyl (TBDMS), and t-butyldiphenylsilyl (TBDPS). A variety of protecting groups for the oxygen and the synthesis thereof may be found in "Protective Groups in Organic Synthesis" by T. W. Greene and P. G. M. Wuts, John Wiley & Sons, 1999.

In the process, compound 1 is contacted with a demethylating agent. In general, the demethylating agent may be a hydrocarbylhaloformate or a N,N-dihydrocarbylformamide. Mixtures of hydrocarbylhaloformates or mixtures of N,N-dihydrocarbylformamides and at least one hydrocarbylhaloformate may also be employed.

In one embodiment, the N-demethylating agent may be a hydrocarbylhaloformate having the formula LC(O)OZ, wherein L and Z are as defined above. In a preferred embodiment utilizing a hydrocarbylhaloformate demethylating agent, L may be chloro or bromo and Z may be methyl, ethyl, propyl, isopropyl, butyl, isobutyl, tert-butyl, phenyl, benzyl, methoxymethyl, vinyl, or 2-chloroethyl. In an exemplary embodiment, the hydrocarbylhaloformate may be a $C_{1-8}$ alkyl chloroformates (e.g., $C_1$ to $C_8$ alkyl), phenyl chloroformate, benzyl chloroformate, or a combination thereof.

In another embodiment, the demethylating agent may be a N,N-dihydrocarbylformamide having the formula $C(O)NZ_2$, Z is as defined above. In an exemplary embodiment, the N,N-dihydrocarbylformamide may be N,N-dimethylformamide, N,N-diethylformamide, N,N-dipropylformamide, N,N-dibutylformamide, N,N-diisobutylformamide, and the like.

To minimize the formation of byproducts, the demethylating agent is preferably maintained in relatively low concentration relative to the N-methyl morphinan substrate. In a batch reaction, for example, this can be achieved by incremental addition of the N-demethylating agent to a reaction mixture containing the N-methyl morphinan substrate. Regardless of whether the reaction is carried out in a batch, continuous, or semi-continuous mode, it is generally preferred that the reaction mixture contain less than about 1 equivalent to about 3 equivalents of the demethylating agent for each equivalent of the N-methyl morphinan substrate.

To facilitate the N-demethylation of the N-methyl morphinan substrate, the reaction is typically carried out in the presence of a proton acceptor. In general, the proton acceptor has a pKa of between about 7 and about 13, preferably between about 8 and about 10. Representative proton acceptors that may be employed include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), organic bases (such as, for example, pyridine, triethylamine, diisopropylethylamine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl) glycine (BICINE), 3-(cyclohexylamino)-1-propanesulfonic acid (CAPS), 2-(cyclohexylamino) ethanesulfonic acid (CHES), 4-(2-hydroxyethyl)-1-piperazinepropanesulfonic acid (EPPS), 4-(2-hydroxyethyl)piperazine-1-ethanesulfonic acid (HEPES), 2-(4-morpholinyl)ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. Where the proton acceptor is an organic buffer, the organic buffer preferably lacks a hydroxy-substituted nitrogen atom, as this substituent may compete for reaction with a hydrocarbylhaloformate reactant. In one embodiment, the proton acceptor is selected from the group consisting of $NaHCO_3$, $KHCO_3$, $K_2CO_3$, NaOH, KOH, and mixtures thereof. In a preferred embodiment, the proton acceptor is $NaHCO_3$, $KHCO_3$, or a combination thereof.

To enable the reaction to proceed at a commercially desirable rate, it is generally preferred that the reaction mixture contain at least about 1 equivalent of proton acceptor for each equivalent of the N-methyl morphinan substrate. In a preferred embodiment, the reaction mixture contains about 1.5 equivalents to about 6 equivalents of proton acceptor per equivalent of N-methyl morphinan substrate. In one particularly preferred embodiment, the reaction mixture contains about 1.5 equivalents to about 3 equivalents of sodium or potassium bicarbonate, or a combined mixture thereof, per equivalent of N-methyl morphinan substrate.

The solvent system for the N-demethylation reaction preferably includes an organic solvent. Representative organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, dichloromethane, cyclohexane, dichloromethane, dichloroethane, diethyl ether, ethyl acetate, fluorobenzene, heptane, hexanes, isobutylmethylketone, isopropyl acetate, methylethylketone, methyltetrahydrofuran, pentyl acetate, n-propyl acetate, tetrahydrofuran, toluene, combinations thereof, and the like. In an exemplary embodiment, the organic solvent may be benzene, chloroform, diethyl ether, ethyl acetate, n-propyl acetate, heptane, hexane, and/or toluene.

In addition to the organic solvent, the solvent system may additionally contain a protic solvent, whereby the solvent system is a two phase, organic phase/protic phase solvent system. Where a two phase, organic/protic solvent system is employed, the solvent system preferably includes water as a protic solvent. In general, water tends to suppress the formation of unwanted side products in the N-demethylation reaction. The solvent may alternatively, or additionally, comprise other protic solvents such as alcohol or other water-miscible solvent; thus, for example, the protic solvent phase may be water, a water/alcohol mixture, or a water/water-miscible solvent mixture. Representative alcohols for the water/alcohol mixture include, for example, methanol, ethanol, isopropyl alcohol, isobutyl alcohol, t-butyl alcohol, n-propyl alcohol, n-butyl alcohol, and combinations thereof. Other water-miscible solvents for the water/water-miscible solvent mixture include, for example, acetonitrile, 1-methyl-2-pyrrolidinone, N,N-dimethylacetamide, N,N-formamide, acetone, tetrahydrofuran, and combinations thereof.

In general, the amount of organic solvent in the solvent system is sufficient to solubilize the N-methyl morphinan substrate, resulting in a substantially homogeneous reaction mixture. The reaction mixture typically includes from about 0.5 equivalents to about 20 equivalents of the organic solvent for each equivalent of the N-methyl morphinan substrate, preferably from about 1 equivalent to about 5 equivalents. Where a two-phase system is employed including water, the water generally occupies from about 0.1% to about 50% of the total reaction volume, preferably from about 1% to about 20%. If present in combination with water, the volume of alcohol or water-miscible solvent is generally from about 0.05% to about 50% of the volume of water, preferably from about 1% to about 10%.

To form the reaction mixture, the N-methyl morphinan substrate is typically combined with the organic solvent (or the two-phase solvent system) prior to the addition of the N-demethylation agent and the proton acceptor. Alternatively, however, the solvent(s), the N-demethylation agent, and the proton acceptor may be combined and thereafter added to the reaction vessel containing the N-methyl morphinan substrate.

The temperature of the reaction mixture for the N-demethylation reaction will typically be within the range of about −40° C. to about 85° C. More typically, the reaction will be carried out at a temperature between about −25° C. and about 65° C. Still more typically, the reaction will be carried out at a temperature of about −20° C. and to about 40° C. In one preferred embodiment, the reaction is carried out at a temperature between about −15° C. and about 40° C., for example, between 0° C. and 40° C. The reaction is typically performed under pressure, and preferably in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of the substrate, and a significantly increased amount of product compared to the amounts of each present at the beginning of the reaction. In general, the reaction proceeds for about 1 hour to about 24 hours, and more typically, for about 2 hours to about 8 hours.

The N-substituted morphinan product (compound 2) may be an N-carboxylic acid ester morphinan compound, wherein $R^6$ is oxygen and n is 1. Alternatively, the N-substituted morphinan product (compound 2) may be an N-carboamide morphinan compound, wherein $R^6$ is nitrogen and n is 2. Compound 2 may be isolated from the reaction mixture by methods known in the art, i.e., for example, by filtration and/or centrifugation. The purity of compound 2 is typically at least 90% as determined by chromatography (e.g., HPLC). In exemplary embodiments, the purity of compound 3 is at least 95%, at least 96%, at least 97%, at least 98%, at least 99%, or greater than 99.5% as determined by chromatography. The yield of compound 2 may range from about 65% to about 95% (mol/mol).

The process described herein may be used to produce a N-substituted morphinan compound that has a (−) or (+) stereochemistry configuration, with respect to the rotation of polarized light. In one embodiment, therefore, the N-methyl morphinan substrate corresponds to formula 1(−) and the N-substituted morphinan product corresponds to formula 2(−):

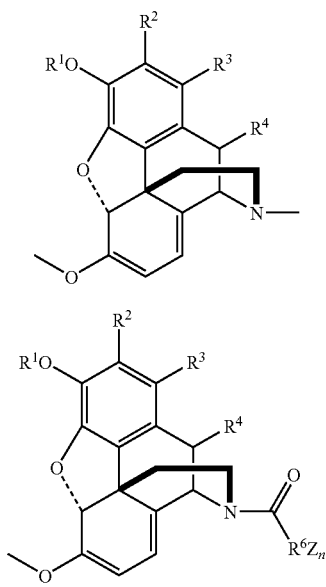

wherein n, $R^1$, $R^2$, $R^3$, $R^4$, $R^6$, and Z are as described above.

In another embodiment, the N-methyl morphinan substrate corresponds to formula 1(+) and the N-substituted morphinan product corresponds to formula 2(+):

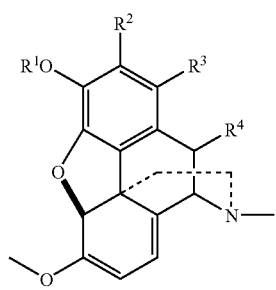

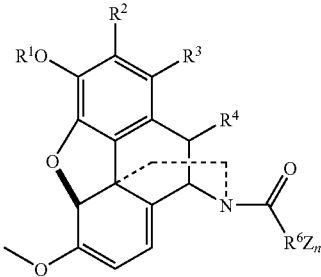

wherein n, $R^1$, $R^2$, $R^3$, $R^4$, $R^6$, and Z are as described above.

In yet another embodiment, the N-methyl morphinan substrate and the N-substituted morphinan product may be an enantiomeric mixture of the respective (−) and (+) enantiomers.

Furthermore, each chiral center of the compounds may have an R or an S configuration. For ease of discussion, the ring atoms of the core morphinan structure referenced herein are numbered as follows:

As illustrated in the core morphinan structure, there are four chiral carbons comprising any of the compounds utilized in the process of the invention, i.e., carbons 5, 13, 14, and 9. Thus, the configuration of the N-methyl morphinan substrate and the N-substituted morphinan product may be RRRS, RRSS, SRRS, SRSS,

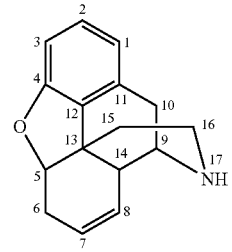

RSRR, RSSR, SSRR, or SSSR, with respect to C(5), C(13), C(14), and C(9). In an exemplary embodiment, the configuration of N-methyl morphinan substrate and the N-substituted morphinan product may be (−)RSRR or (+)SRSS.

II. Further Derivatization

The N-substituted morphinan products of the present invention may be end products themselves, or intermediates that may be further derivatized in one or more steps to yield further morphinan intermediates or end products. For instance, the N-carboxylic acid ester morphinan compound may be subsequently converted to commonly utilized normorphinan intermediates, such as noroxymorphone and noroxycodone which, in turn, may be further derivatized to form other commercially valuable morphinan compounds (e.g., buprenorphine, dihydroetorphine, diprenorphine, etorphine, nalbuphene, nalmefene, naloxone, and naltrexone. General reaction schemes for the preparation of such commercially valuable morphinans are disclosed, among other places, in U.S. Pat. No. 4,368,326 to Rice, the entire disclosure of which is hereby incorporated by reference herein. As previously described, the N-carboxylic acid ester morphinan product used as a starting material for this further derivatization may be the (−) enantiomer, the (+) enantiomer, or an enantiomeric mixture of the two.

For purposes of illustration, Reaction Scheme 2 depicts the preparation of noroxymorphone (9) from N-carboxylic acid ester nororipavine (7) and Reaction Scheme 3 depicts the preparation of noroxycodone (10) from N-carboxylic acid ester northebaine (4), wherein $R_{311}$ is an oxygen protecting group and Z is as defined above in connection with Reaction Scheme 1.

Reaction Scheme 2

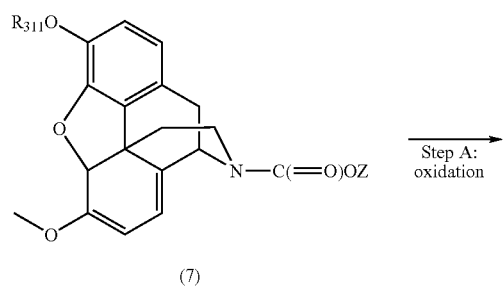

(7)

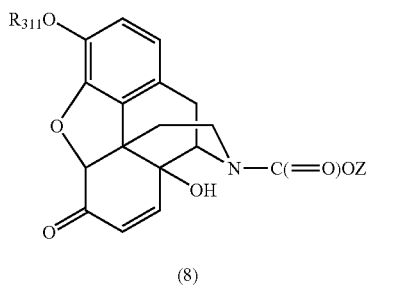

(8)

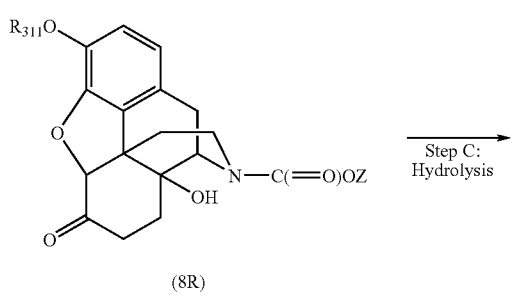

(8R)

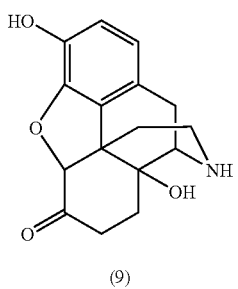

(9)

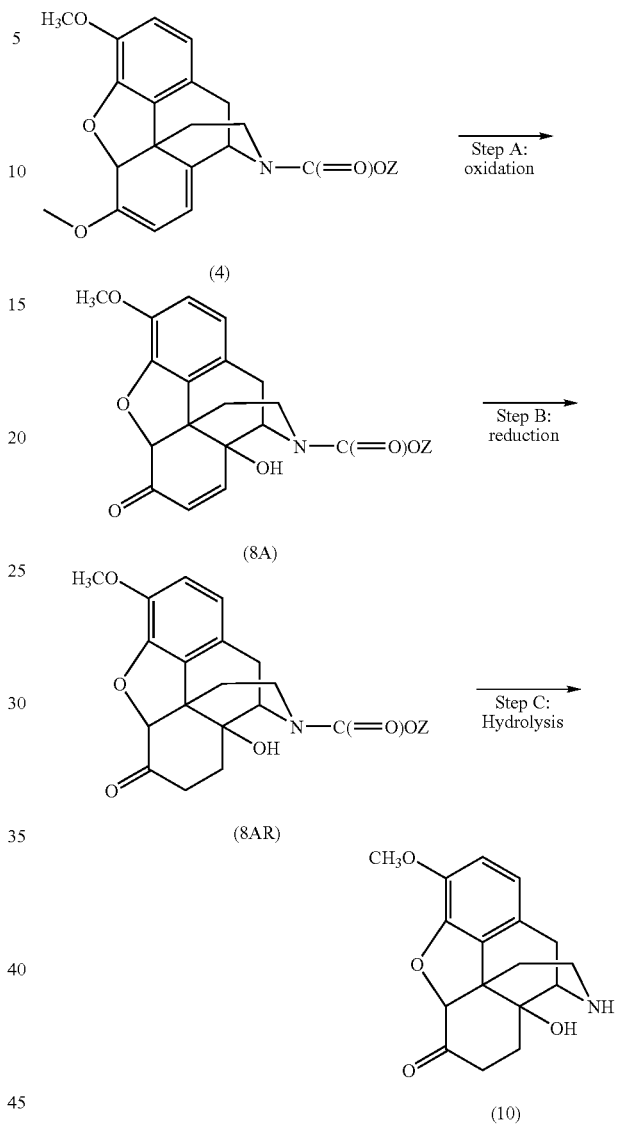

As shown in Reaction Schemes 2 and 3, Step A involves the oxidation of the N-carboxylic acid ester odpavine (7) or N-carboxylic acid ester northebaine (4) to form an α,β-unsaturated morphinan-6-one (8) or (8A). In general, the oxidation involves the treatment of the N-carboxylic acid ester oripavine (7) or N-carboxylic acid ester northebaine (4) with an oxidizing agent. A variety of oxidizing agents may be used in this step for the oxidation of the C(6) and the C(14) positions of the N-carboxylic acid ester oripavine (7) or N-carboxylic acid ester northebaine (4). Examples of oxidizing agents that may be used include, but are not limited to, dichromates (e.g., ammonium dichromate, potassium dichromate, sodium dichromate, and the like); bromates (e.g., barium bromate, magnesium bromate, potassium bromate, sodium bromate, and the like); chlorates (e.g., ammonium chlorate, barium chlorate, calcium chlorate, potassium chlorate, sodium chlorate, and the like); chlorates (e.g., copper chlorite, lead chlorite, potassium chlorite, sodium chlorite, and the like); chloroisocyanuric acids (e.g., trichloroisocyanuric acid, and the like); chromates (e.g., potassium chromate, and the like); chromium oxides (e.g., chromic anhydride (chromium trioxide)); dichromates (e.g., sodium dichromate, potassium dichromate, and the like); hydrogen peroxide; hypobromites (e.g., sodium hypobromite, and the like); hypochlorites (e.g., calcium hypochlorite, potassium hypochlorite, sodium hypochlorite, and the like); hypoiodites (e.g., sodium hypoiodite, potassium hypoiodite, and the like); inorganic peroxides (e.g., barium peroxide, calcium peroxide, cesium peroxide, lithium peroxide, magnesium peroxide, potassium peroxide, rubidium peroxide, sodium peroxide, strontium peroxide, and the like); iodates (e.g., calcium iodate, potassium iodate, sodium iodate, zinc iodate, and the like); iodine oxides (e.g., diiodine pentaoxide, and the like); lead oxides (e.g., lead dioxde, and the like); manganese dioxide; nitrates (e.g., ammonium nitrate, ammonium cerium nitrate, barium nitrate, potassium nitrate, silver nitrate, sodium nitrate, and the like); nitric acid; nitrites (e.g., potassium nitrite, sodium nitrite, and the like); perchlorates (e.g., ammonium perchlorate, potassium perchlorate, sodium perchlorate, and the like); periodates (e.g., potassium periodate, sodium periodate, and the like); periodic acids (e.g., metaperiodic acid, and the like); permanganates (e.g., ammonium permanganate, magnesium permanganate, potassium permanganate, sodium permanganate, and the like); peroxoborates (e.g., ammonium peroxoborate, and the like); perchloric acid; peroxodisulfates (e.g., ammonium peroxodisulfates, potassium peroxydisulfate, and the like); peroxyacids (e.g., peroxyacetic acid, peroxybenzoic acid, peroxyformic acid, trifluoroperacetic acid, and the like); organic peroxides (e.g., benzoyl peroxide, and the like); tetroxides (e.g., osmium tetroxide, ruthenium tetroxide, and the like); and oxygen. As the oxygen source, air may also be used-. In one particular embodiment, the oxidizing agent is a peroxyacid; thus, for example, the oxidizing agent may be peroxyacetic acid, peroxybenzoic acid, peroxyformic acid, or trifluoroperacetic acid. Typically, a slight excess of the oxidizing agent is employed.

In Step B of Reaction Schemes 2 and 3, the α,β-unsaturated morphinan-6-one (8) or (8A) is reduced to form compound 8R or compound 8AR, respectively. Generally, the reduction is carried out to reduce the α,β-unsaturation between the C(7) and the C(8) ring carbon atoms and to remove the carboxylic acid ester moiety (—C(O)OZ) from the nitrogen atom. Depending on the particular substituents, i.e., depending upon the nature of $R_{311}$ and Z, additional treatment of the compound with a hydrolyzing agent may be performed to remove the hydroxy protecting group, $R_{311}$, and the carboxylic acid ester moiety, —C(O)OZ.

A wide variety of reducing approaches may be employed in Step B including, for example, chemical reduction, catalytic reduction, and the like. Representative reducing agents for use in chemical reduction include hydrides (e.g., hydrogen iodide, hydrogen sulfide, lithium aluminum hydride, sodium borohydride, sodium cyanoborohydride, and the like), or combinations of a metal (e.g., tin, zinc, or iron) or a metal compound (e.g., chromium chloride, chromium acetate, and the like) with an organic or inorganic acid (e.g., formic acid, acetic acid, propionic acid, trifluoroacetic acid, p-toluenesulfonic acid, hydrochloric acid, and the like), samarium iodide, and others. Representative reducing agents for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. In one particular embodiment, the α,β-unsaturated morphinan-6-one (8) or (8A) is reduced using catalytic reduction (e.g., Pd/C catalyzed transfer hydrogenation).

Step C of Reaction Schemes 2 and 3 involves a hydrolysis reaction to form noroxymorphone (9) or noroxycodone (10). Where a hydrolyzing agent is used to assist in the removal of the hydroxy protecting group, $R_{311}$, and/or the carboxylic acid ester moiety, —C(O)OZ, a variety of aqueous hydrolyzing agents may be employed, provided the particular hydrolyzing agent selected does not affect any other positions or bonds present on the morphinan. In general, conventional hydrolyzing agents may be employed, such as sulfuric acid, phosphoric acid, methanesulfonic acid, trifluoroacetic acid, p-toluenesulfonic acid, benzenesulfonic acid, trifluoromethanesulfonic acid, hydrochloric acid, or hydrobromic acid.

Those of skill in the art will appreciate that other N-substituted morphinan products may be derivatized to other intermediate or end products using Steps A, B, and C, as outlined above in Reaction Schemes 2 and 3, or using other derivatization methods known in the art.

Other end product and intermediate morphinans of interest that may be derived from N-carboxylic acid ester morphinan products from Reaction Scheme 1 include a wide range of opiate receptor agonists and antagonists, and intermediates thereof, generally corresponding to Formula (100):

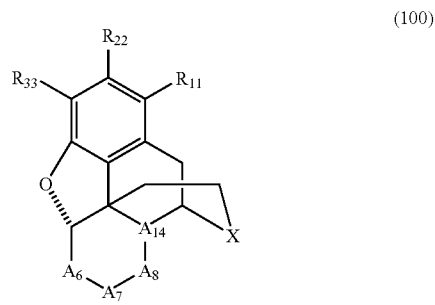

(100)

wherein -$A_6$-$A_7$-$A_8$-$A_{14}$- corresponds to Formulae (S), (T), (U), (V), (W), (X), (Y), or (Z):

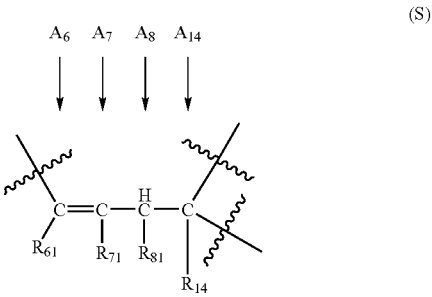

(S)

-continued

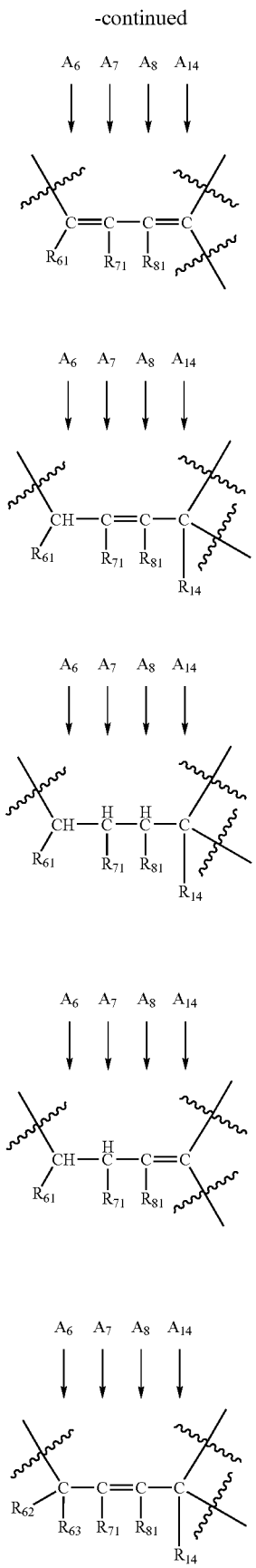

(T)
(U)
(V)
(W)
(X)

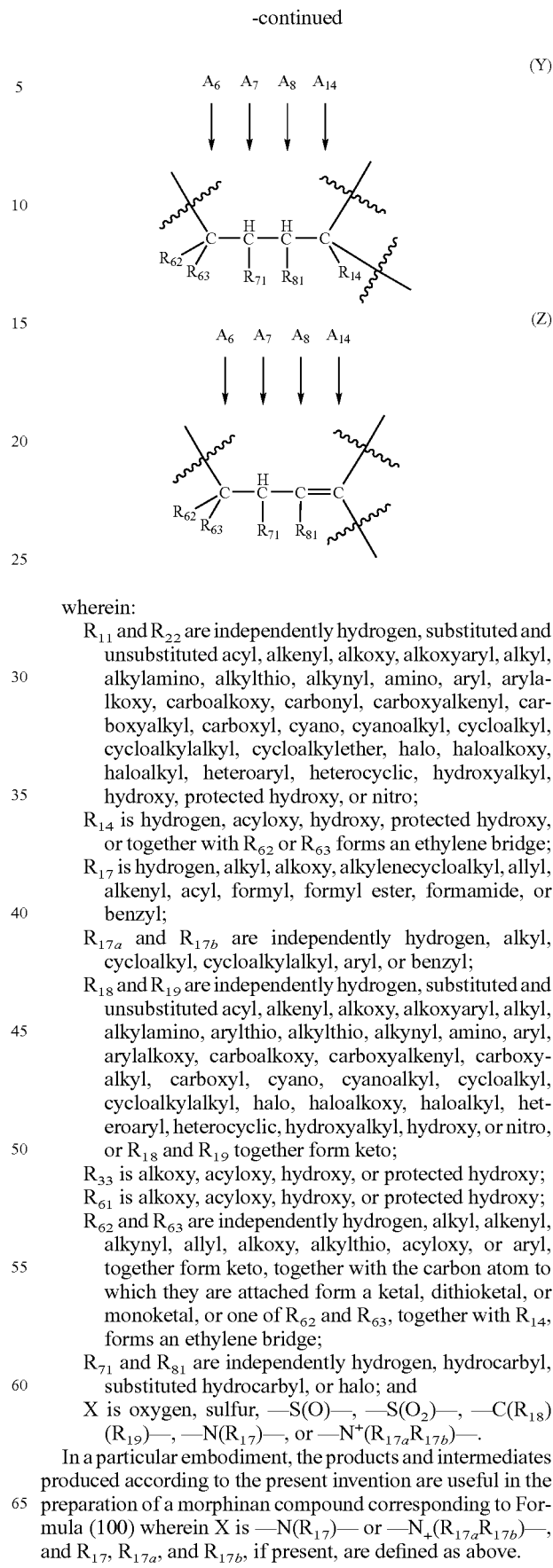

-continued (Y)
(Z)

wherein:
$R_{11}$ and $R_{22}$ are independently hydrogen, substituted and unsubstituted acyl, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxy, protected hydroxy, or nitro;

$R_{14}$ is hydrogen, acyloxy, hydroxy, protected hydroxy, or together with $R_{62}$ or $R_{63}$ forms an ethylene bridge;

$R_{17}$ is hydrogen, alkyl, alkoxy, alkylenecycloalkyl, allyl, alkenyl, acyl, formyl, formyl ester, formamide, or benzyl;

$R_{17a}$ and $R_{17b}$ are independently hydrogen, alkyl, cycloalkyl, cycloalkylalkyl, aryl, or benzyl;

$R_{18}$ and $R_{19}$ are independently hydrogen, substituted and unsubstituted acyl, alkenyl, alkoxy, alkoxyaryl, alkyl, alkylamino, arylthio, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, halo, haloalkoxy, haloalkyl, heteroaryl, heterocyclic, hydroxyalkyl, hydroxy, or nitro, or $R_{18}$ and $R_{19}$ together form keto;

$R_{33}$ is alkoxy, acyloxy, hydroxy, or protected hydroxy;

$R_{61}$ is alkoxy, acyloxy, hydroxy, or protected hydroxy;

$R_{62}$ and $R_{63}$ are independently hydrogen, alkyl, alkenyl, alkynyl, allyl, alkoxy, alkylthio, acyloxy, or aryl, together form keto, together with the carbon atom to which they are attached form a ketal, dithioketal, or monoketal, or one of $R_{62}$ and $R_{63}$, together with $R_{14}$, forms an ethylene bridge;

$R_{71}$ and $R_{81}$ are independently hydrogen, hydrocarbyl, substituted hydrocarbyl, or halo; and X is oxygen, sulfur, —S(O)—, —S(O$_2$)—, —C(R$_{18}$)(R$_{19}$)—, —N(R$_{17}$)—, or —N$^+$(R$_{17a}$R$_{17b}$)—.

In a particular embodiment, the products and intermediates produced according to the present invention are useful in the preparation of a morphinan compound corresponding to Formula (100) wherein X is —N(R$_{17}$)— or —N$_+$(R$_{17a}$R$_{17b}$)—, and $R_{17}$, $R_{17a}$, and $R_{17b}$, if present, are defined as above.

For purposes of clarity, the carbon atoms of Formulae (S), (T), (U), (V), (W), (X), (Y), and (Z) corresponding to $A_6$, $A_7$, $A_8$, and $A_{14}$ of Formula (100), respectively, have been identified (by indicating with an arrow which carbon atom corresponds to each). Further, wavy lines have been included in Formulae (S), (T), (U), (V), (W), (X), (Y), and (Z) to indicate the points of attachment to the polycyclic ring of Formula (100).

As previously noted in connection with Reaction Schemes 2 and 3, exemplary intermediate morphinans that may be produced include, for example, noroxymorphone (i.e., Formula (100) wherein $R_{11}$, $R_{17}$, and $R_{22}$ are hydrogen, $R_{33}$ is hydroxy, X is —N($R_{17}$)—, and -$A_6$-$A_7$-$A_8$-$A_{14}$- corresponds to Formula (Y) wherein $R_{14}$ is hydroxy, $R_{62}$ and $R_{63}$ together form keto, and $R_7$, and $R_8$, are hydrogen) (which corresponds to Formula (101) below) and noroxycodone (i.e., Formula (100) wherein $R_{11}$, $R_{17}$, and $R_{22}$ are hydrogen, $R_{33}$ is methoxy, X is —N($R_{17}$)—, and -$A_6$-$A_7$-$A_8$-$A_{14}$- corresponds to Formula (Y) wherein $R_{14}$ is hydroxy, $R_{62}$ and $R_{63}$ together form keto, and $R_{71}$ and $R_{81}$ are hydrogen) (which corresponds to Formula (102) below), and salts, intermediates, and analogs thereof.

Exemplary end product morphinans that may be derived from noroxymorphone, noroxycodone, or otherwise from N-carboxylic acid ester morphinan (2) of Reaction Scheme 1 include, for example, nalbuphine, nalmefene, naloxone, naltrexone, naltrexone methobromide, 3-0-methyl naltrexone, and the salts, intermediates, and analogs thereof. Exemplary examples are presented below:

(101)

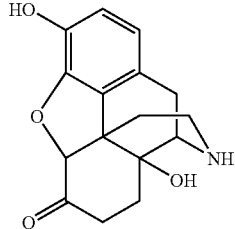

noroxymorphone (102)

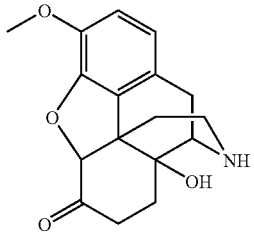

noroxycodone (103)

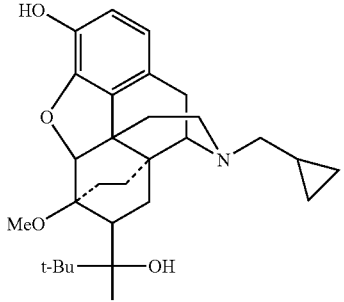

buprenorphine

-continued (104)

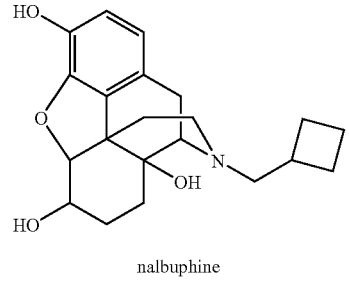

nalbuphine (105)

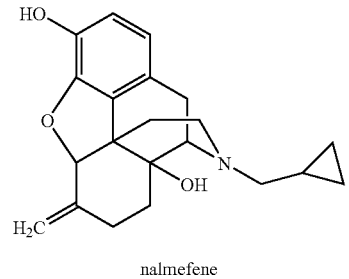

nalmefene (106)

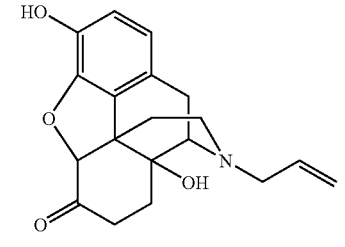

naloxone (107)

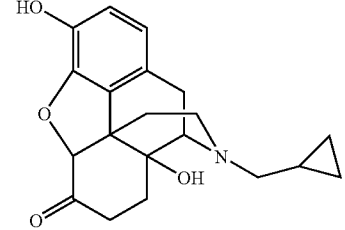

naltrexone (108)

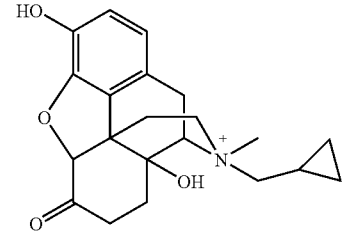

naltrexone methobromide

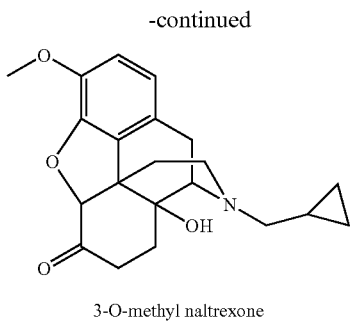

3-O-methyl naltrexone

Definitions

The term "acyl," as used herein alone or as part of another group, denotes the moiety formed by removal of the hydroxy group from the group COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, or heterocyclo, and $R_2$ is hydrogen, hydrocarbyl or substituted hydrocarbyl.

The term "acetal," as used herein, refers to a moiety in which two bonded oxygens are to the same carbon; one of the other R groups of an acetal carbon is hydrogen.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkaryl" or "alkylaryl" as used herein describes groups which are preferably aryl groups having a lower alkyl substituent, such as toluyl, ethylphenyl, or methylnapthyl.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aralkyl" as used herein describes groups which are preferably lower alkyl containing from one to eight carbon atoms having an aryl substituent, such as benzyl, phenylethyl, or 2-napthylmethyl.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "ether," as used herein, denotes an oxygen atom connected to two alkyl, aryl, substituted alkyl, or substituted aryl groups, i.e., of the general formula ROR'.

The terms "halogen" or "halo" as used herein alone or as part of another group refer to chlorine, bromine, fluorine, and iodine atoms.

The term "heteroatom" refers to atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

The terms "oxygen protecting group" as used herein denote a group capable of protecting a free oxygen atom (i.e., the oxygen of a hydroxyl group) that, subsequent to the reaction for which protection is employed, may be removed without disturbing the remainder of the molecule.

The term "silyl ether," as used herein, denotes a moiety in which a silicon atom is covalently bonded to an alkoxy group. The general structure is $R^1R^2R^3Si$—O—$R^4$, wherein $R^4$ is an alkyl group or an aryl group, and $R^1$-$R^3$ are independently hydrocarbyl or substituted hydrocarbyl.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various iterations of the invention.

Example 1

Reaction of Oripavine with Ethyl Chloroformate

Oripavine was reacted with three different concentrations of ethyl chloroformate ($ClCO_2Et$). Three samples of oripavine were prepared. For each, 0.3 g of oripavine was added to 5 mL of chloroform ($CHCl_3$) with stirring. Once in solution, the mixtures were cooled to about 0-5° C. Five mL of saturated $NaHCO_3$ was added with stirring to each mixture. A different amount of $ClCO_2Et$ was added to each mixture, i.e., 1, 2 or 3 equivalents of $ClCO_2Et$ (as shown in Table 1). Each mixture was stirred for 30 minutes at room temperature after addition of the ethyl chloroformate and then sampled for HPLC to determine if the reaction has gone to completion.

TABLE 1

Oripavine Reaction.

| Sample # | $ClCO_2Et$ | Result |
|---|---|---|
| 1 | 95 µL | Reaction not complete |
| 2 | 2 × 95 µL | Reaction not complete |
| 3 | 3 × 95 µL | Reaction complete |

As shown in Table 1, the reaction was complete when oripavine was reacted with three equivalents of $ClCO_2Et$ (sample #3). For this sample, the organic solution was washed with 5% $NaHCO_3$ (9 mL), 5% HOAc (9 mL), and then water (9 mL). The organic layer was reduced to dryness under a partial vacuum to give 0.4 g of solid.

Example 2

Reaction of Thebaine with Ethyl Chloroformate

To determine the correct ratio for thebaine and ethyl chloroformate an experiment similar to that described in Example 1 was performed. For each sample, 0.31 g of thebaine was dissolved in 5 mL of $CHCl_3$. Once in solution, the mixtures were cooled to about 0-5° C. Five mL of saturated $NaHCO_3$ was added with stirring to each mixture. $ClCO_2Et$ (as shown in Table 2) was added to each mixture, which were stirred for 30 minutes at room temperature and then sampled for HPLC to determine if the reaction has gone to completion.

TABLE 2

Thebaine Reaction.

| Sample # | $ClCO_2Et$ | Result |
|---|---|---|
| 1 | 95 µL | Reaction not complete |
| 2 | 2 × 95 µL | Reaction not complete |
| 3 | 3 × 95 µL | Reaction complete |

As shown in Table 2, the reaction was complete when thebaine was reacted with three equivalents of $ClCO_2Et$ (sample #3). This sample was washed with 5% $NaHCO_3$, 5% HOAc, and water as described above. The organic layer was reduced to dryness under a partial vacuum to give 0.4 g of solid.

What is claimed is:

1. A process comprising: preparing a compound of Formula 2 from a compound of Formula 1 according to the following reaction scheme:

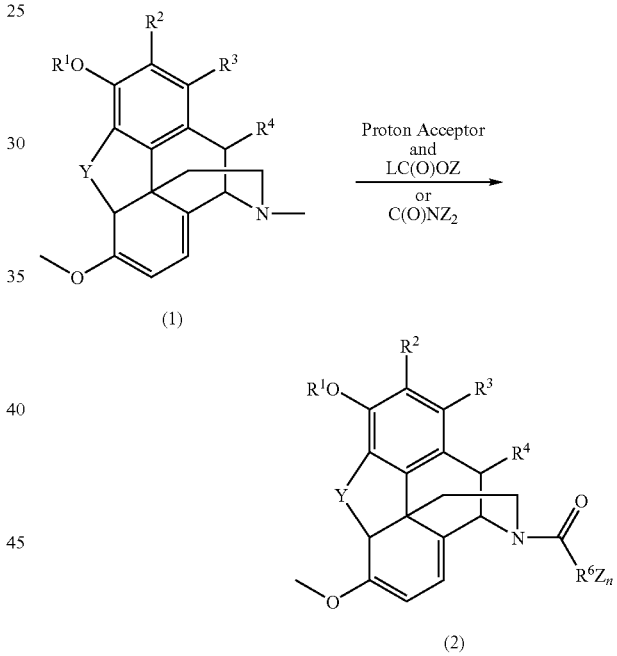

wherein:
$R^1$ is selected from the group consisting of hydrogen, alkyl, alkenyl, aryl, substituted alkyl, substituted alkenyl, substituted aryl, acyl, alkoxycarbonyl, acetal, ether, silyl ether, alkylsulfonyl, and an oxygen protecting group;
$R^2$, $R^3$, and $R^4$ are independently selected from the group consisting of hydrogen, halogen, hydroxyl, {—}$OR^8$, acyl, alkyl, alkenyl, aryl, substituted alkyl, substituted alkenyl, substituted aryl, and alkoxycarbonyl;
$R^6$ is an atom selected from the group consisting of oxygen and nitrogen;
$R^8$ is selected from the group consisting of hydrocarbyl and substituted hydrocarbyl;
L is halogen;
Y is an atom selected from the group consisting of oxygen, nitrogen and sulfur;

Z is selected from the group consisting of alkyl, alkenyl, alkylaryl, aralkyl, aryl, substituted alkyl, substituted alkenyl, substituted alkylaryl, substituted aralkyl, and substituted aryl; and n is 1 or 2.

2. The process of claim 1, wherein:

L is selected from the group consisting of bromo and chloro; and

Y is oxygen.

3. The process of claim 2, wherein Z is selected from the group consisting of methyl, ethyl, propyl, isopropyl, butyl, isobutyl, tert-butyl, phenyl, benryl, methoxymethyl, vinyl, or 2-chloroethyl.

4. The process of claim 1, wherein

Y is oxygen; $R^2$, $R^3$, and $R^4$ are each hydrogen; and Z is selected from the group consisting of alkyl and benzyl.

5. The process of claim 4, wherein $R^6$ is oxygen and n is 1.

6. The process of claim 4, wherein $R^6$ is nitrogen and n is 2.

7. The process of claim 1, wherein LC(O)OZ is a hydrocarbylhaloformate selected from the group consisting of a $C_{1-8}$alkyl chloroformate, phenyl chloroformate, benzyl chloroformate, and a combination thereof.

8. The process of claim 1, wherein $C(O)NZ_2$ is a N,N-dihydrocarbylformamide selected from the group consisting of N,N-dimethylformamide, N,N-diethylformamide, N,N-dipropylformamide, N,N-dibutylformamide, N,N-diisobutylformamide, and a mixture thereof.

9. The process of claim 1, wherein the molar ratio of LC(O)OZ or $C(O)NZ_2$ to the compound comprising Formula 1 is from about 1:1 to about 3:1; the proton acceptor has a pKa greater than about 7 and is selected from the group consisting of $NaHCO_3$, $KHCO_3$, $Na_2CO_3$, $K_2CO_3$, NaOH, KOH, and combinations thereof; and the molar ratio of the proton acceptor to the compound comprising Formula 1 is from about 1.5:1 to about 6:1.

10. The process of claim 1, wherein the reaction is conducted in the presence of a solvent system.

11. The process of claim 10, wherein the solvent system comprises an organic solvent selected from the group consisting of benzene, chloroform, diethyl ether, ethyl acetate, n-propyl acetate, heptane, hexane, toluene, and a combination thereof; and the molar ratio of organic solvent to the compound comprising Formula 1 is from about 0.5:1 to about 20:1.

12. The process of claim 11, wherein the solvent system further comprises a protic solvent selected from the group consisting of water, methanol, ethanol, isopropyl alcohol, isobutyl alcohol, t-butyl alcohol, n-propyl alcohol, n-butyl alcohol, and a combination thereof.

13. The process of claim 11, wherein the solvent system further comprises a water-miscible solvent selected from the group consisting of water, acetonitrile, 1-methyl-2-pyrrolidinone, N,N-dimethylacetamide, N,N-formamide, acetone, tetrahydrofuran, and a combination thereof.

14. The process of claim 1, wherein the reaction is conducted at a temperature ranging from about 0° C. to about 40° C.

15. The process of claim 1, wherein the yield of the compound comprising Formula 2 is from about 65% to about 95%.

16. The process of claim 1, wherein the optical activity of compounds comprising Formulas 1 and 2 is selected from the group consisting of (−) enantiomer, (+) enantiomer, and a combination thereof.

17. The process of claim 1, wherein the configuration of carbons 5, 13, 14, and 9, respectively, of compounds comprising Formulas 1 and 2 is selected from the group consisting RRRS, RRSS, SRRS, SRSS, RSRR, RSSR, SSRR, and SSSR.

18. An N-carboxylic acid ester morphinan derivative compound of Formula 2:

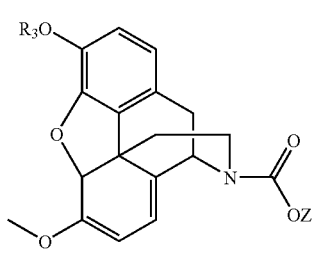

(2)

wherein $R_3$ is —C(O)OZ and Z is selected from the group consisting of methyl, ethyl, propyl, isopropyl, butyl, isobutyl, tert-butyl, phenyl, benzyl, methoxymethyl, vinyl, and 2-chloroethyl.

* * * * *